US007595149B1

(12) United States Patent
Anderson et al.

(10) Patent No.: US 7,595,149 B1
(45) Date of Patent: Sep. 29, 2009

(54) METHODS FOR CANCER DETECTION

(75) Inventors: Kimberly W. Anderson, Georgetown, KY (US); Kimberly M. L. May, Union, NJ (US); Leonidas G. Bachas, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 11/269,363

(22) Filed: Nov. 8, 2005

Related U.S. Application Data

(60) Provisional application No. 60/625,875, filed on Nov. 8, 2004.

(51) Int. Cl.
*C12Q 1/00* (2006.01)
*C12N 5/02* (2006.01)
(52) U.S. Cl. .......................... 435/4; 435/7.21; 435/325
(58) Field of Classification Search ........................ None
See application file for complete search history.

(56) References Cited

U.S. PATENT DOCUMENTS

| | | | |
|---|---|---|---|
| 5,177,012 | A | 1/1993 | Kim et al. |
| 5,942,385 | A | 8/1999 | Hirth |
| 6,262,337 | B1 | 7/2001 | von Euler et al. |
| 6,331,301 | B1 | 12/2001 | Eriksson et al. |
| 6,383,484 | B1 | 5/2002 | Achen et al. |
| 6,642,009 | B2 | 11/2003 | Hung |
| 6,689,580 | B1 | 2/2004 | Achen et al. |
| 6,730,489 | B1 | 5/2004 | Achen et al. |
| 6,770,179 | B1 | 8/2004 | Nanci |
| 6,787,323 | B2 | 9/2004 | Batley et al. |
| 6,855,508 | B2 | 2/2005 | Fei et al. |
| 6,867,005 | B2 | 3/2005 | Keys et al. |
| 6,884,879 | B1 | 4/2005 | Baca et al. |
| 6,887,468 | B1 | 5/2005 | Thorpe et al. |
| 2002/0051974 | A1 | 5/2002 | Dodge et al. |
| 2002/0081637 | A1 | 6/2002 | Li et al. |
| 2002/0102260 | A1 | 8/2002 | Achen et al. |
| 2002/0119153 | A1 | 8/2002 | Thorpe et al. |
| 2002/0164624 | A1 | 11/2002 | Debinski et al. |
| 2002/0164663 | A1 | 11/2002 | Fuqua et al. |
| 2003/0044865 | A1 | 3/2003 | Fei et al. |
| 2003/0157523 | A1 | 8/2003 | Frantz et al. |
| 2003/0175276 | A1 | 9/2003 | Thorpe et al. |
| 2003/0176674 | A1 | 9/2003 | Rosen et al. |
| 2003/0232400 | A1 | 12/2003 | Radka et al. |
| 2004/0175730 | A1 | 9/2004 | Achen et al. |
| 2005/0095657 | A1 | 5/2005 | Arbiser et al. |

FOREIGN PATENT DOCUMENTS

EP      1519193      3/2005

WO      WO 01/88520      11/2001

OTHER PUBLICATIONS

Freshney, R.I. Culture of Animal Cells, A Manual of Basic Technique, Alan R. Liss, Inc. 1983, New York, p. 4.*
Dermer, G.B. Another anniversary for the war on cancer. Bio/technology, 1994. vol. 12, p. 320.*
May, K.M.L., Vogt, A., Bachas, L.G., and Anderson, K.W. Vascular endothelial growth factor as a biomarker for the early detection of cancer using a whole cell-based biosensor. Analytical and bioanalytical chemistry, 2005. vol. 382, pp. 1010-1016.*
May, K.M.L., Wang, Y., Bachas, L.G., and Anderson, K.W. Development of a whole-cell-based biosensor for detecting histamine as a model toxin. Analytical Chemistry, 2004. vol. 76, pp. 4156-4161.*
Stina Haggstrom et al. "Vascular Endothelial Growth Factor Content in Metastasizing and Nonmetastasizing Dunning Prostatic Adenocarcinoma," The Prostate 45:42-50 (2000).
Petri Salven et al. "High Pre-Treatment Serum Level of Vascular Endothelial Growth Factor (VEGF) is Associated with Poor Outcome in Small-Cell Lung Cancer," Int. J. Cancer (Pred. Oncol.): 79, 144-146 (1998).
Duque et al., "Plasma Levels of Vascular Endothelial Growth Factor are Increased in Patients with Metastatic Prostate Cancer," Elsevier Science Inc., Urology 54 (3),1999, pp. 523-527.
Stockton et al., "p-21-activated Kinase Regulates Endothelial Permeability through Modulation of Contractility," The Journal of Biological Chemistry, vol. 279, No. 45, Issue of Nov. 5, pp. 46621-46630, 2004, The American Society for Biochemistry and Molecular Biology, Inc.
Jiang et al., "Hepatocyte Growth Factor/Scatter Factor Decreases the Expression of Occludin and Transendothelial Resistance (TER) and Increases Paracellular Permeability in Human Vascular Endothelial Cells," Journal of Cellular Physiology 181:319-329 (1999).
Granato et al., "Basic fibroblast growth factor and vascular endothelial growth factor serum levels in breast cancer patients and healthy women: useful as diagnostic tools?," Breast Cancer Research, vol. 6 No. 1, 2004, pp. R38-R45.

(Continued)

*Primary Examiner*—Larry R. Helms
*Assistant Examiner*—Lei Yao
(74) *Attorney, Agent, or Firm*—King & Schickli, PLLC

(57) ABSTRACT

A method is provided for detecting an analyte indicative of a cancer or a metastatic disease condition, which utilizes the ability of the analyte to induce permeability in a barrier. The method includes providing a biosensor having a barrier which is substantially impermeable to an ion, a permeable membrane which is selective for the ion, and a detector capable of detecting the ion. The biosensor is contacted with a sample including at least one of the ion and the analyte, wherein the analyte causes at least a portion of the ion to pass through the barrier and the membrane. Passage of the ion through the barrier and membrane allows detection of the ion, providing indirect detection of the analyte. In one embodiment, the barrier is a cell monolayer, the membrane is selective for potassium, and the analyte is vascular endothelial cell growth factor.

16 Claims, 4 Drawing Sheets

OTHER PUBLICATIONS

Sliutz et al., "Serum evaluation of basic fibroblast growth factor in cervical cancer patients," Elsevier Science Ireland Ltd., Cancer Letters 94 (1995) 227-231.

Sezer et al., "Serum levels of the angiogenic cytokines basic fibroblast growth factor (bFGF), vascular endothelial growth factor (VEGF) and hepatocyte growth factor (HGF) in multiple myeloma," European Journal of Haematology 2001: 66, pp. 83-88.

Fuhrmann-Benzakein et al., "Elevated Levels of Angiogenic Cytokines in the Plasma of Cancer Patients," Int. J. Cancer: 85, 40-45 (2000).

Walsh et al., "Modulation of tight junction structure and function by cytokines," Elsevier Science B.V., Advanced Drug Delivery Reviews 41 (2000) 303-313.

* cited by examiner

Fig. 3a
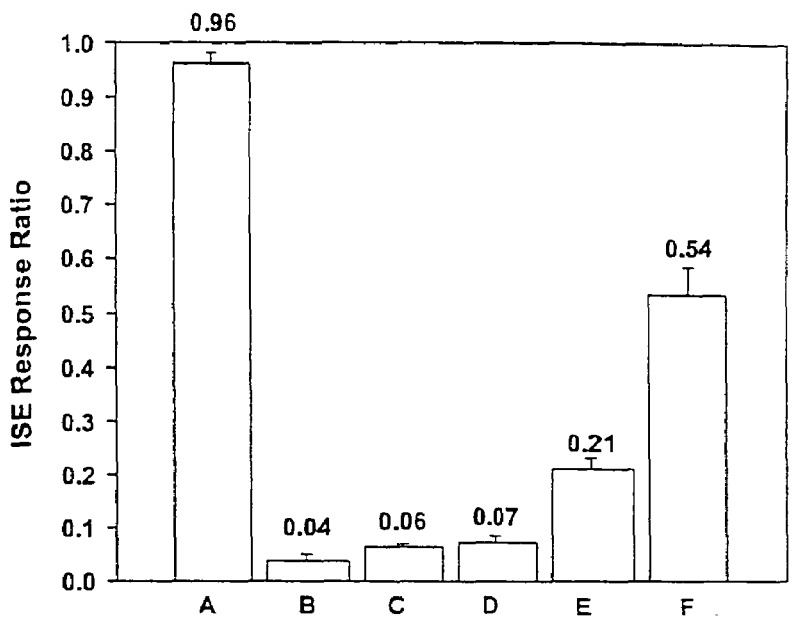
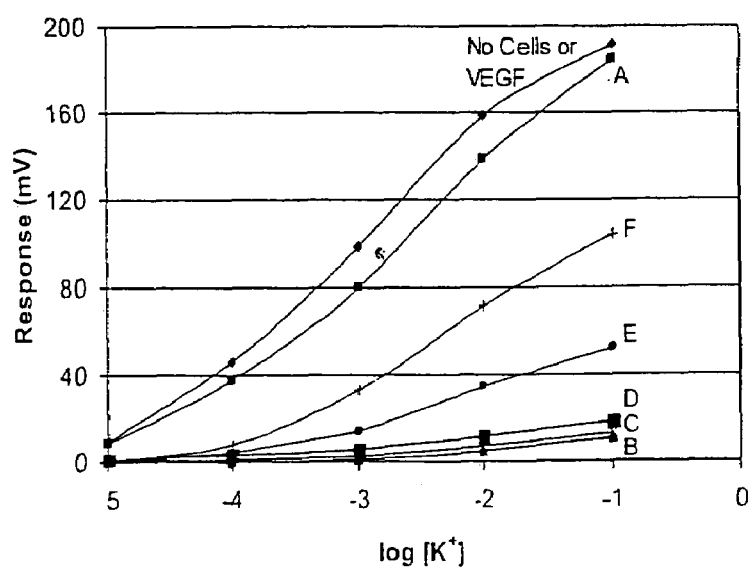
Fig. 3b

METHODS FOR CANCER DETECTION

This application claims the benefit of Provisional Patent Application Ser. No. 60/625,875 filed on Nov. 8, 2004, the disclosure of which is incorporated herein in its entirety by reference.

TECHNICAL FIELD

The present invention relates to methods for early detection of cancer, and for monitoring progression, metastasis, and/or treatment efficacy of cancer. In particular, the invention provides a method for detection of cancer comprising detection of analytes indicative of cancer or a metastatic disease using a biosensor.

BACKGROUND OF THE INVENTION

It is known that early detection of cancer is highly correlated with patient survival. Accordingly, research has focused on the discovery and recognition of new diagnostic biomarkers that relate to the presence of cancer, its severity, and its subsequent progression. Certain biomarkers are specific to certain cancer types, i.e., prostate specific antigen as a diagnostic marker for prostate cancer. However, other, non-specific biomarkers have value in early detection of cancer, determination of prognosis, monitoring of effectiveness of cancer treatment, detection of recurrence post-treatment, and the like. In this respect, it is known that various cytokines, growth factors, toxins, chemokines, and hormones are found in elevated concentrations at the onset of cancer and during metastasis of cancer.

One such cytokine is vascular endothelial cell growth factor (VEGF), also called vascular permeability factor (VPF). Vascular endothelial cell growth factor is an endothelial cell mitogen, and is known to be present in very small quantities in normal human blood in order to facilitate activities such as wound healing. In contrast, soluble VEGF is released in large quantities by tumorigenic cells (e.g. carcinomas of the breast, large and small intestine, pancreas, kidney, and the like) due to its critical role in angiogenesis. During angiogenesis, new blood vessels form from existing vessels to supply nutrients to the developing tumor cells. Due to VEGF's mitogenic nature, it facilitates the formation of the new blood vessels by selective action on endothelial cells.

Quantities of VEGF in serum and plasma of patients with tumors from a multitude of cancers (small-cell lung cancer, primary breast cancer, non-Hodgkin's lymphoma, prostate cancer, and the like) have been found to be significantly elevated. The concentration of VEGF has also been correlated with the presence of metastatic disease, disease stage in colorectal cancer, and poor prognosis in patients with small cell lung cancer.

Conventional assays for cytokines such as VEGF for use in detecting, diagnosing, or monitoring the progress or prognosis of cancer, or for monitoring treatment efficacy, generally rely on specific immunological assays for the protein. However, there is a need in the art for a more rapid screening method for early detection and monitoring of cancer. The screening method should be simple, reliable, and allow detection of indices of cancer such as VEGF and other analytes known to be produced in elevated quantities during onset, progression, and metastasis of various cancers.

The present invention satisfies this need in the art by providing methods and systems for detecting and monitoring cancer and its progression via detection and quantitation of a cytokine using a whole-cell biosensor. The invention relies on induction of permeability in the cell portion of the biosensor to detect and quantitate the cytokine.

SUMMARY OF THE INVENTION

In accordance with the purposes of the present invention as described herein, in one aspect of the invention a method is provided for detecting an analyte indicative of a cancer or a metastatic disease condition, comprising providing a biosensor comprising a barrier which is substantially impermeable to an ion, a permeable membrane which is selective for the ion, and a detector capable of detecting the ion. The biosensor is contacted with a sample including at least one of the ion and an analyte indicative of a cancer or a metastatic disease condition, wherein the analyte causes at least a portion of the ion to pass through the barrier and the membrane to allow detection of the presence or absence of the ion and thereby indirect detection of the presence or absence of the analyte.

The barrier is a live cell layer known to be responsive to the analyte being detected. In one embodiment of the invention, the barrier is a transformed human endothelial cell line, and the analyte is VEGF. The cell barrier is typically provided as a substantially confluent cell monolayer which is contiguous with the permeable membrane. In use, the cell monolayer is substantially impermeable to the ion, but becomes at least partially permeable to the ion upon contact with the analyte. The detector may be coupled to a transducer to provide a measurable signal upon detection of the ion.

The analyte being detected will typically be selected such that the amount of the analyte in the sample is indicative of the presence, progression, or severity of a cancer or a metastatic disease condition, or of the efficacy of a treatment therefor. The analyte may be selected from the group of cancer-related analytes consisting of cytokines, growth factors, hormones, chemokines, and toxins, including but not limited to tumor necrosis factor, basic fibroblast growth factor, interleukin 6, interleukin 8, hepatocyte growth factor, or any permeability modifying agent released by cancer, and combinations thereof. In one embodiment, the analyte detected is VEGF.

The membrane of the biosensor may be selected to be natively selective for the ion of choice, or may be chemically modified for selectivity for the ion. The permeable membrane may be chemically modifyied using an ionophore to induce selectivity for the ion. In one embodiment, a permeable cellulose triacetate membrane is modified with valinomycin to induce selectivity for potassium.

In another aspect of the present invention, a method is provided for monitoring the presence, progression or severity of a cancer or a metastatic disease, or the efficacy of a treatment therefor, in a patient during a predetermined time interval, comprising the steps of (1) obtaining a biological sample from a patient having or at risk of having a cancer or a metastatic disease, (2) combining the biological sample with a predetermined amount of an ion to form a mixture, (3) contacting the mixture with a biosensor as described above, (4) detecting the presence or absence of an analyte which is indicative of a cancer or a metastatic disease condition in the mixture, wherein the analyte causes the live cell barrier to become at least partially permeable to the ion whereby the ion is detected by the detector, (5) correlating the amount of the ion detected with the quantity of the analyte in the biological sample, and (6) repeating steps 1 through 5 over time to measure the progress of the cancer or the treatment. It will be appreciated that if the sample naturally contains a known, fixed concentration of the ion, inclusion of additional amounts of the ion is unnecessary.

The biological sample may be selected from the group consisting of serum, whole blood, plasma, saliva, tears, milk, urine, other biological/physiological fluids, a tissue biopsy, an organ biopsy, lymphatic fluid, and any combination thereof. The quantity of the analyte detected in the biological sample may be then correlated with the presence, progress, or severity of the cancer or metastatic disease, or with the efficacy of the treatment. The biosensor used in this method is substantially as described above. In one embodiment, the present method comprises use of a biosensor as described above, comprising a human umbilical vascular endothelial cell line grown on a cellulose triacetate membrane chemically modified with valinomycin to induce potassium selectivity. The biosensor is used to detect and quantify VEGF in the biological samples.

In yet another aspect of the present invention, a system for detecting the presence of an analyte indicative of a cancer or a metastatic disease condition, comprising a cell-based biosensor, an ion, and at least one standard sample containing a predetermined quantity of an analyte indicative of a cancer or a metastatic disease condition. In one possible embodiment, the cell-based biosensor comprises a monolayer of human umbilical endothelial cells on a cellulose triacetate membrane modified for potassium selectivity. The ion is potassium, and the analyte is VEGF. The biosensor includes an electrode supporting the membrane, with the electrode coupled to a transducer which provides a signal which can be detected upon detection of the ion by the electrode.

It should be appreciated that the embodiments shown and described herein are illustrations of some of the modes best suited to carry out the invention. It will be realized that the invention is capable of other different embodiments and its several details are capable of modification in various, obvious aspects all without departing from the invention. Accordingly, the drawings and descriptions will be regarded as illustrative in nature, and not as restrictive.

BRIEF DESCRIPTION OF THE DRAWINGS

The accompanying drawings incorporated in and forming a part of the specification, illustrate several aspects of the present invention and together with the description serve to explain the principles of the invention. In the drawings:

FIG. 3 shows the biosensor response under various conditions: FIG. 3a shows the ratio of the electrode response obtained at 0.1 M KCl following treatment to the response for the membrane without cells or VEGF at 0.1 M KCl. Experimental conditions were (A) 1 µg/ml VEGF only, (B) cells only, (C) 1 µg/ml VEGF for 2 hr, (D) 1 µg/ml VEGF for 4 hr, (E) 1 µg/ml VEGF for 5 hr, (F) 1 µg/ml VEGF for 6 hr (error bars represent SEM); FIG. 3b shows calibration curves for the biosensor under conditions A-F above, with the top line representing the average biosensor response without cells or VEGF;

Reference will now be made in detail to the present preferred embodiment of the invention, an example of which is illustrated in the accompanying drawings.

DETAILED DESCRIPTION OF THE INVENTION

Conventional methods of cancer detection and monitoring often rely on detection of specific biomarkers which may be diagnostic of specific types of cancer. However, it is known that blood concentrations of various cytokines and growth factors, while not necessarily diagnostic of specific cancers, can be correlated to early stages of cancer, to likelihood and/or aggressiveness of metastasis, and to efficacy of cancer treatment.

It was considered that a method of rapid screening for such cancer-related analytes would be useful as a general method of monitoring presence of cancer, effectiveness of cancer therapy, determination of prognosis, and/or likelihood of recurrence. Accordingly, a biosensor-mediated method for early detection of cancer, or for monitoring the progress and/or treatment efficacy of a cancer or a metastatic disease, was developed. As an example, VEGF, a multiple-isoform glycoprotein which is a known endothelial cell mitogen, is present even during the early stages of cancer and is released in soluble form by tumorigenic cells due to its vital role in angiogenesis [Ferrara (2004) *Endocrine Reviews* 25, 581-611; incorporated herein by reference]. Therefore, in one embodiment of the invention, the biosensor utilizes the ability of VEGF to induce permeability of a human endothelial cell line monolayer, passage of an ion therethrough, and detection of the ion, as an indirect detection method for the analyte.

Figure 1:
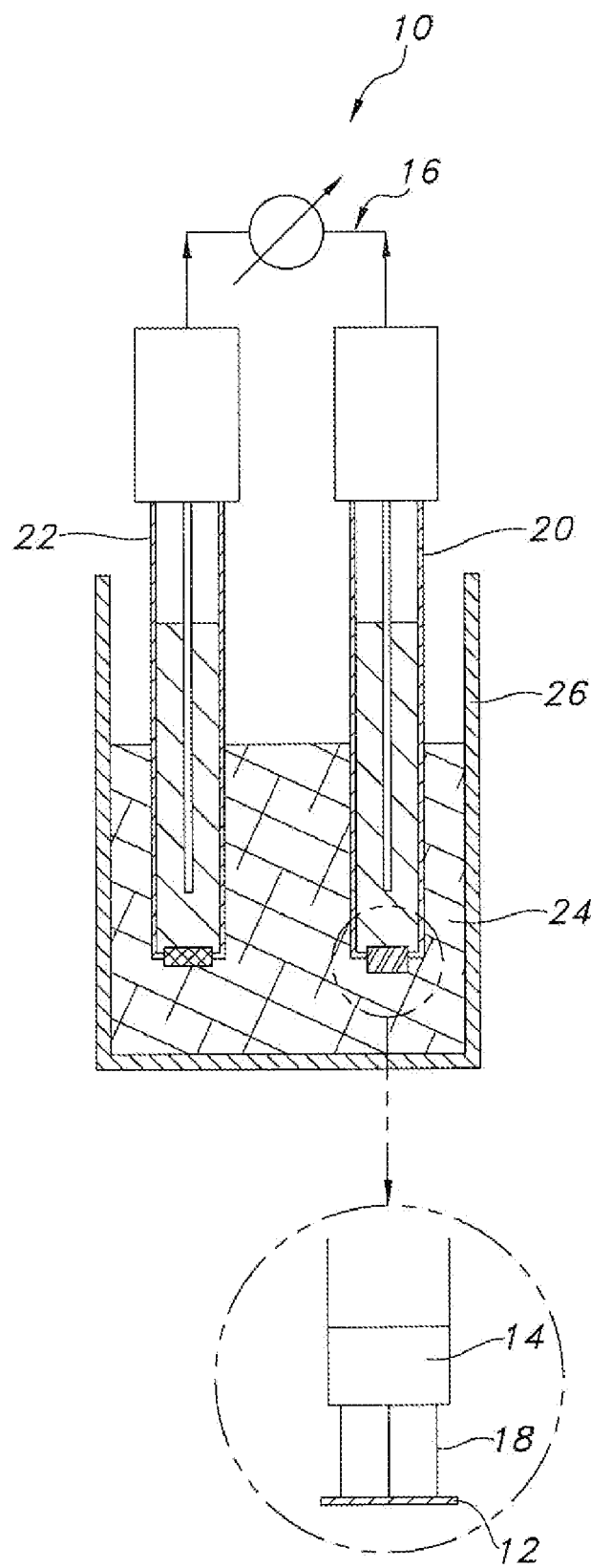
FIG. 1 schematically depicts an embodiment of the biosensor of the present invention.

In one embodiment, depicted in FIG. 1, the biosensor 10 utilized in the method of the present invention comprises a barrier 12 which is substantially impermeable to an ion, a permeable membrane 14 which is selective for the ion, and a detector 16 capable of detecting the ion. In the depicted embodiment, the barrier 12 is a human umbilical vein endothelial cell monolayer coupled to an ion-selective cellulose triacetate membrane 14 by a linker molecule 18. The barrier 12/membrane 14 complex is carried by the detector 16 to provide an ion-selective electrode 20 as will be described in greater detail below. A reference electrode 22 may also be provided as part of the detector 16 as is known in this art to allow detection of a potentiometric difference in response to detection of the ion.

A sample 24, contained in a receptacle 26, may be contacted with the biosensor 10, wherein the sample 24 includes at least one of the ion and an analyte of interest. It will be appreciated that the analyte will typically be indicative of a cancer and/or a metastatic disease condition, and further causes at least a portion of the ion to pass through the barrier 12 and the permeable membrane 14 to be detected by the detector 16.

The following examples are presented in support of and to further illustrate the invention as described herein. However, the invention is not to be considered as limited thereto.

Example 1

Figure 2:
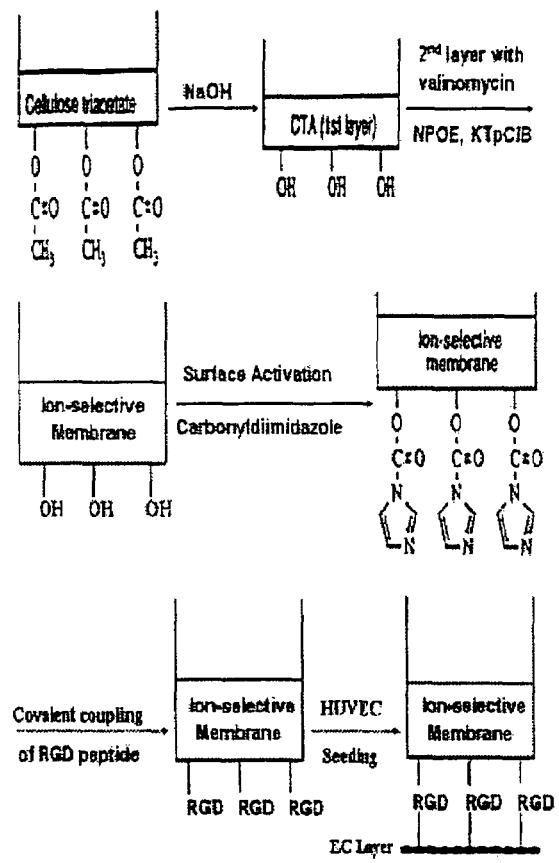
FIG. 2 shows the preparation of a modified ion-selective cellulose triacetate membrane (selective for potassium) and attachment of a HUVEC monolayer.

Referring to FIG. 2, a cellulose triacetate (CTA; Eastman Kodak, Rochester, N.Y.) membrane was prepared as an ion-selective support for a cell layer. The base layer of the membrane was prepared by dissolving 74 mg of CTA pellets in 1.1 mL of methylene chloride (Aldrich, Milwaukee, Wis.), 0.4 mL of chloroform (Aldrich), and 0.40 mL of 1,1,2,2-tetrachloroethane (Aldrich). The mixed solution was then cast in a 31 mm i.d. glass ring placed on a TEFLON plate. After solvent evaporation, the membrane was removed and floated on 1.0 M sodium hydroxide for 4.5 hr. Raised edges of the membrane ensured that only the lower surface of the membrane was hydrolyzed to provide free OH groups. The membrane was then rinsed with deionized water.

A second membrane layer was cast using an ionophore cocktail to induce selectivity for potassium. The ionophore cocktail consisted of 1 mg of valinomycin (Calbiochem, San Diego, Calif.), a plasticizer (100 µL of o-nitrophenyl octyl ether; Fluka, Ronkonkoma, N.Y.), and a lipophilic salt (0.42 mg potassium tetrakis(chlorophenyl)borate; Fluka) with 35 mg of CTA. The mixture was dissolved in a solvent mixture composed of 0.80 mL of methylene chloride and 0.80 mL of chloroform. The solvent was allowed to evaporate for 2 days as the two membrane layers fused into a single asymmetric membrane.

The bottom side of the basic membrane (having the free OH groups) was immersed in cold deionized water. Next, 324 mg of carbonyldiimidazole (CDI; Sigma, St. Louis, Mo.) was added in increments over a 15 min period, giving a final concentration of 0.10 M CDI to activate the surface for peptide coupling. The membrane was then immediately incubated overnight in a 0.1 M sodium carbonate solution (pH 9.5) containing 400 µg of a synthetic RGD peptide sequence (Bachem, King of Prussia, Pa.) to promote cell binding to the membranes. The peptide sequence used was Gly-Arg-Gly-Asp-Ser (GRGDS) to promote covalent peptide attachment from the N-terminal amine. This is because the arg-gly-asp (RGD) segment of fibronectin is one of the most widely recognized protein sequences to which human umbilical vein endothelial cells (HUVECs) bind. The membranes were then rinsed sequentially with 0.10 M $NaHCO_3$, deionized water, acetate buffer (pH 4.0), and deionized water. Protein immobilization was confirmed using a micro-BCA protein assay (Pierce Biotechnology, Rockford, Ill.).

Six mm i.d. disks cut from the membranes prepared as described above were mounted onto Philips IS-561 electrode bodies (Glasblaserei Möller, Zurich) with the RGD-modified surface of the membrane facing the sample solution. Human umbilical vein endothelial cells (Cambrex BioScience, East Rutherford, N.J.) were cultured in an EGM-2 media (Cambrex BioScience) supplemented with fetal bovine serum, hydrocortisone, insulin-like growth factor, basic fibroblast growth factor, VEGF, human epidermal growth factor, ascorbic acid, human fibroblast growth factor, gentamicin sulfate, amphotericin-B, and heparin. The HUVECs were used experimentally up to passage 5. The HUVECs were seeded onto the bottom surface of the electrode-mounted membrane disks at a density of $1 \times 11^5$ cells/mL. The cells were allowed to spread and form a confluent monolayer over the membrane surface for 24 h at 37° C. in a humidified incubator with 5% $CO_2$.

The internal filling solution for the electrode was 0.01 M KCl, and the internal reference electrode was Ag/AgCl. The external reference electrode was a double-junction Ag/AgCl electrode (Orion Model 90-02-00) with an Orion (90-02-02) internal filling solution and 0.1 M Tris buffer (pH 7.5) in the outer compartment. Potentiometric responses were measured with a four-channel high impedance amplifier interface (World Precision Instruments) connected to a Model 100 Instrunet A/D converter. Data were analyzed using Instrunet software on a Macintosh Power PC. Prior to initial use, the electrodes were conditioned in sterile 0.1 M KCl solution. Calibration plots were constructed by plotting the measured potential (mV) versus the logarithm of the concentration of potassium ions present in the bulk solution.

Example 2

Figure 4:
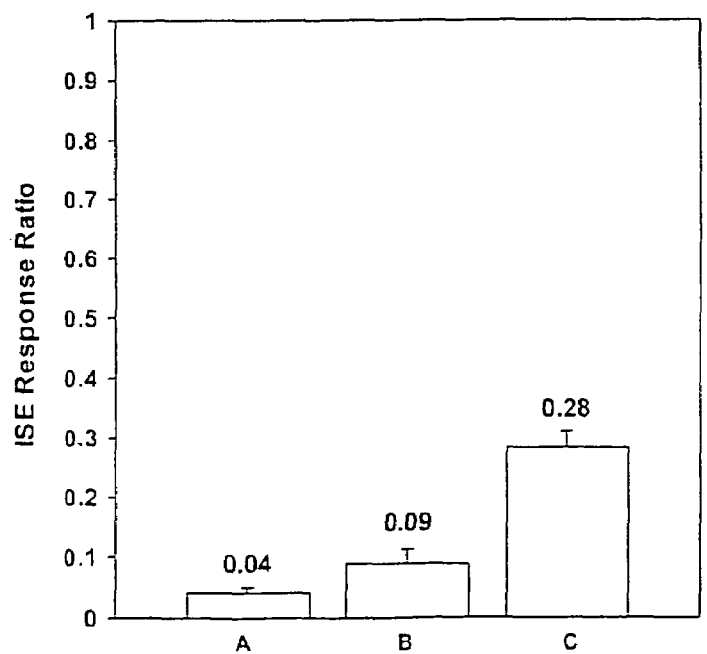
FIG. 4 shows the ratio of the biosensor response following exposure to 100 ng/ml VEGF to the response for the biosensor without cells or VEGF. Experimental conditions were (A) cells only, (B) after 6 hr exposure, and (C) after 8 hr exposure (error bars represent SEM)
Figure 5:
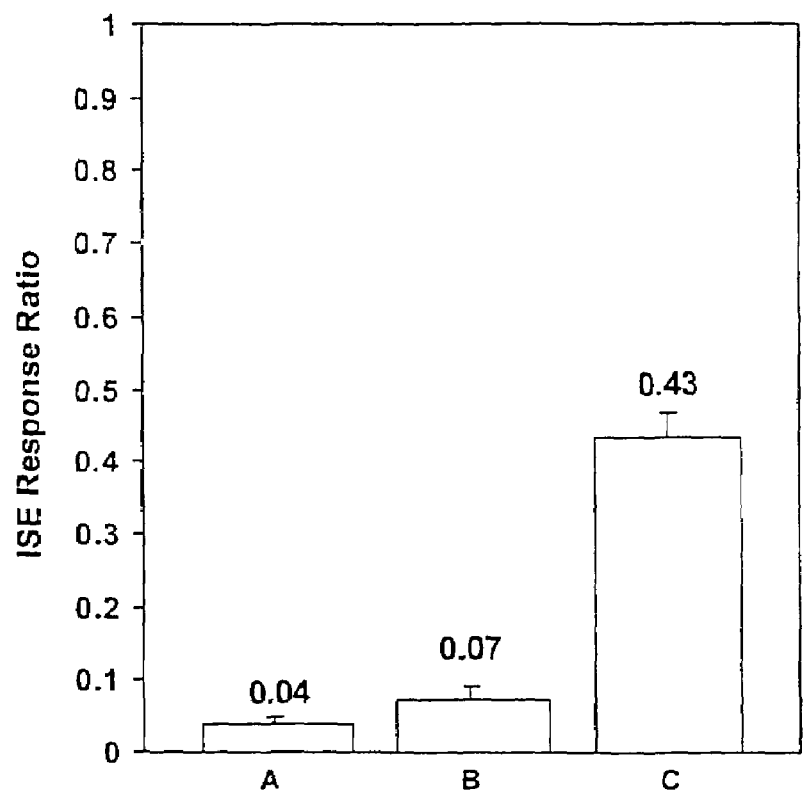
FIG. 5 shows the ratio of the biosensor response obtained at 0.1 M KCl following exposure to 1 ng/ml VEGF to the response for the biosensor without cells or VEGF. Experimental conditions were (A) cells only, (B) after 8 hr exposure, and (C) after 10 hr exposure (error bars represent SEM)

The response of the biosensor as described in Example 1 was first evaluated after protein immobilization and as a function of cell confluency. After confirmation of the inhibited response following 24 h of cell growth (i.e., diminished transport of potassium through the confluent monolayer), the cell-based membranes were exposed to concentrations of VEGF ranging from 100 pg/mL to 1 µg/mL (pH 7.0 in 0.1% BSA in PBS) for times ranging from 2 to 10 hr. The biosensor response was measured for the following conditions at a final concentration of 0.1 M. KCl: (1) membrane without cells or VEGF exposure to confirm that the membrane response was not affected by RGD; (2) membrane without cells and with VEGF (1 µg/mL) to confirm that the highest concentration of VEGF did not affect the response in the absence of HUVECs (FIGS. 3a, 4, and 5); (3) membrane with cells and without VEGF to confirm the inhibited sensor response after 24 h of cell growth (FIGS. 3a, 4, and 5); and (4) membrane with cells and with varying concentrations of VEGF at different exposure times. Data were reported as a ratio of the potential response for ion-selective electrodes (ISEs) with HUVECs and/or VEGF to the potential response of the ISEs without HUVECs or VEGF for a final concentration of 0.1 M KCl to account for slight variations between fabricated membranes. Three to five replicates were performed for each VEGF concentration.

Response of the biosensor to a high concentration of VEGF (1 µg/mL) was evaluated. Referring to FIG. 3, no significant response from the sensor was obtained at 2 and 4 hr of exposure. Increasing the exposure time to 5 hr significantly increased the response, and at 6 hr of exposure the response was nearly double that of the 5 hr response period. Calibration curves for each exposure time supported these findings (FIG. 3b).

It was desired also to evaluate the lower detection limit of the sensor. The biosensor of Example 1 was exposed to a reduced concentration (100 ng/ml) of VEGF. Experimental conditions were substantially as described previously. The response ratio was very low after exposing the biosensor to 100 ng/ml of VEGF for 6 hr, but approximately tripled after 8 hr (FIG. 4). Reducing the VEGF concentration to 1 ng/ml with an 8 hr exposure period resulted in a response ratio nearly equal to the control response (monolayer without VEGF). However, increasing the response time to 10 hr significantly increased the response ratio (FIG. 5).

Example 3

Figure 6:
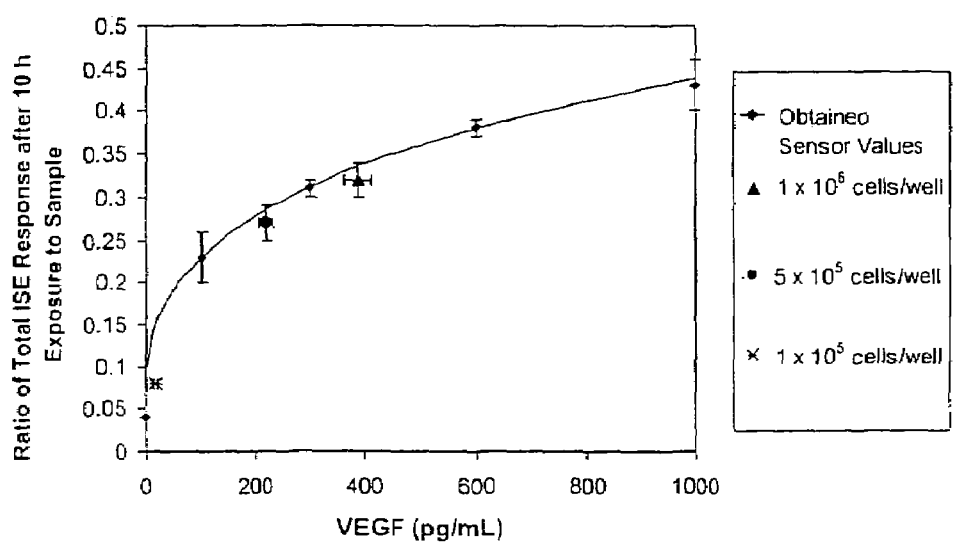
FIG. 6 shows the ratio of the biosensor response obtained at 0.1 M KCl following 10 hr exposure to VEGF concentrations ranging from 0 to 1,000 pg/ml, with the data fitted using TableCurve 2D v5.01; also shown are the biosensor responses to media aspirated from metastatic melanoma cell cultures (1205LU) at seeding densities of $1 \times 10^6$, $5 \times 10^5$, and $1 \times 10^5$ cells/well; all results are plotted against the average concentration of VEGF as measured by ELISA for the same samples.

The response ratio from the biosensor was evaluated as a function of the concentration of VEGF. The sensor was exposed to increasing concentrations (100, 300, and 600 pg/ml) of VEGF, over a 10 hr exposure period based on the results described in Example 2. Referring to FIG. 6 (see the plot of "Obtained sensor values"), as the concentration of VEGF increased, the response ratio also increased. The curve shape was characteristic of binding events showing a rapid binding rate at lower cytokine concentrations, and reaching saturation at higher cytokine concentrations. Based on these data, the detection limit for the biosensor under these conditions was estimated to be 70 pg/ml.

Example 4

Detection of unknown concentrations of VEGF produced by cell lines was evaluated also. For comparison, a conventional immunoassay for VEGF was used to detect VEGF in the samples. The medium was assayed for VEGF using a Human Quantikine VEGF ELISA kit (R & D Systems, Minneapolis, Minn.) according to the manufacturer's instructions. Samples were analyzed at 450 nm using an $El_x$ Universal Microplate Reader (Bio-Tek Instruments) with three replicates per cell line. Data are reported as mean concentration (pg/ml)±SEM. Tu2% medium and MelM medium (see below) were also assayed as controls.

Human epidermal melanocytes (HEMs; ScienCell, San Diego, Calif.) were cultured in MelM media (ScienCell) as controls. Subculturing reagents were trypsin/EDTA, TNS, and PBS. WM793 nonmetastatic melanoma cells (not expected to produce significant quantities of VEGF) and 1205LU metastatic melanoma cells (expected to produce VEGF) were obtained from the laboratory of Dr. David Kaetzel, University of Kentucky. These cells were cultured in TU2% medium consising of MCDB 153 medium powder (Sigma), Leibovitz's L-15 medium powder (Gibco, Invitrogen Corp.), FBS (Sigma), bovine insulin, sodium bicarbonate, and calcium chloride. Subculturing reagents were trypsin/EDTA and PBS.

The cell lines were cultured for 48 hr (growth) in test wells at various densities, and supernatant was withdrawn. Initial cell density was controlled in each test well, and the final cell count was determined to confirm that the growth rate of the cells was consistent over the 48 hr period. After 48 hr of growth, the biosensor was exposed to the supernatant medium for 10 hr as described in Example 4.

Concurrently, a VEGF ELISA was performed on the same supernatant medium samples. The ELISA results for the 1205LU (metastatic) cells were plotted against the biosensor response ratio (FIG. 6) to evaluate how closely the biosensor predicted the VEGF concentration as measured by ELISA. The data points for the ELISA assay fell within the standard errors of the plot representing the biosensor model except at the lowest concentrations of VEGF.

VEGF concentrations determined by the biosensor method and by ELISA are shown in Table 1. For the metastatic cell line (1205LU) at higher cell seeding densities ($1\times10^6$ and $5\times10^5$ cells/well), the biosensor gave results comparable to ELISA. The biosensor substantially predicted actual VEGF concentrations as measured by ELISA, and was shown to respond to VEGF concentrations corresponding to documented concentrations of VEGF found in blood of cancer patients [Haggstrom et al. (2000) Prostate 45:42-50; Salven et al. (1998) Cancer 79:144-146; Duque et al. (1999) Urology 54:523-527 (all incorporated herein in their entirety by reference)]. Table 1 also shows that the nonmetastatic (WM 793) cells produced no detectable VEGF as measured by ELISA. Similarly, the biosensor results were within the range seen in the control studies (see FIGS. 3-5). By way of confirmation, normal HEMs produced no detectable VEGF by ELISA assay, and the biosensor produced no appreciable response.

TABLE 1

Comparison of in vitro VEGF production by various cell types.

| | Seeding density (cells/well) | Final concentration (cells/ml) | ELISA concentration (pg/ml) | Response ratio from biosensor | Predicted concentration from sensor (pg/ml) |
|---|---|---|---|---|---|
| 1205LU | $1 \times 10^6$ | $1.1 \times 10^6$ | 387 ± 25 | 0.32 ± 0.02 | 339 ± 80 |
| | $5 \times 10^5$ | $4.2 \times 10^5$ | 220 ± 15 | 0.27 ± 0.02 | 189 ± 54 |
| | $1 \times 10^5$ | $2.4 \times 10^5$ | 17.4 ± 3.7 | 0.08 ± 0 | 0.86 ± 0.4 |
| WM793 | $1 \times 10^6$ | $9.2 \times 10^5$ | ND | 0.03 ± 0.01 | 0 |
| | $5 \times 10^5$ | $4.0 \times 10^5$ | ND | 0.04 ± 0.01 | 0 |
| | $1 \times 10^5$ | $2.1 \times 10^5$ | ND | 0.05 ± 0.02 | 0 |
| HEMs | $1 \times 10^5$ | $5.3 \times 10^5$ | ND | 0.04 ± 0 | 0 |
| TU2% | N/A | N/A | ND | 0.04 | 0 |
| MelM | N/A | N/A | ND | 0.05 | 0 |
| HUVEC | N/A | N/A | NM | 0.05 | 0 |
| 0.1 w/v % BSA in PBS | N/A | N/A | NM | 0.04 | 0 |

Data presented as means ± SEM.
ND = not detectable.
NM = not measured.

Accordingly, it has been shown that the biosensor of the present invention has a detection limit of at least 70 pg/ml. Using the molecular weight of $VEGF_{165}$ (42 kDa), this corresponds to a $2\times10^{-12}$ M detection limit. The biosensor can therefore be used to effectively screen for quantities of VEGF in biological samples, such as for example blood samples, from cancer patients. Since it is known that VEGF levels in biological samples, including serum and plasma, are correlated with the presence, metastasis, and disease stage of cancer (Haggstrom et al., 2000; Salven et al., 1998; Duque et al., 1999), the biosensor of the present invention can be used to effectively screen for cancer.

In comparison to conventional screening procedures such as biopsies, the method of the present invention is adaptable for use in a minimally invasive manner, and could be used as an early cancer screening tool by a physician during a routine office visit. Further, the method of the present invention provides the further advantage of a rapid response time (10 hr or less), in comparison to a conventional biopsy procedure, which may take a week or more to schedule, perform the procedure, and report the results to the patient.

The foregoing description of the preferred embodiment of this invention has been presented for purposes of illustration and description. It is not intended to be exhaustive or to limit the invention to the precise form disclosed. Obvious modifications or variations are possible in light of the above teachings. It will be appreciated by the skilled artisan that the method may be adapted to a variety of combinations of cell types, analytes, and ions used in the biosensor, with the proviso that the analyte or analytes be indicative or predictive of a cancer, and that permeability is induced in the particular cell type used. For example, different cell types could be incorporated into the biosensor of the invention, either alone or in combination, such as native endothelial cells, keratinocytes, lung cells, kidney cells, and the like, with the proviso that the cells form a layer that is substantially impervious to passage of the ion of choice absent contact with a permeability-inducing analyte.

Alternative membrane types are also contemplated by the present invention, including polymer membranes such as polyurethane, poly-(hydroxyethyl)methacrylate, poly(vinyl) chloride, and the like, which may be utilized in order to improve cell adhesion or alter the mechanism of attachment of the bridging linker, with the proviso that the membrane is or can be made selective for the ion of choice.

Still further, it will be appreciated that the detected molecule need not be an ion, but may be any ionic or neutral molecule, with the proviso that the sensor is able to detect the molecule and the membrane is appropriately selective for the molecule.

Still yet further, multiple biosensors comprising different cell types and membrane types, each being more or less sensitive to the presence of a particular cancer-inducing analyte, may be incorporated into a sensor array adapted for detection of multiple combinations of analytes, such as for example a combination of VEGF, tumor necrosis factor, and interleukin 8, to facilitate complete sample analysis and improve the predictive value of the method.

The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for detecting an analyte, comprising:
   providing a biosensor comprising a live endothelial or epithelial cell barrier which is substantially impermeable to a potassium ion, a permeable membrane which is selective for the potassium ion, and a detector capable of detecting the potassium ion;
   contacting the biosensor with a sample including at least one of the potassium ion and an analyte selected from at least one of a vascular endothelial growth factor, a basic fibroblast growth factor, a hepatocyte growth factor, and a tumor necrosis factor-α, wherein the analyte induces permeability of the live cell barrier and causes at least a portion of the potassium ion to pass through the live cell barrier and the membrane; and
   detecting the presence or absence of the potassium ion.

2. The method of claim 1, wherein the live cell barrier is a transformed human endothelial cell line.

3. The method of claim 2, wherein the live cell barrier is provided as a substantially confluent cell monolayer which is contiguous with the permeable membrane.

4. The method of claim 3, wherein the cell monolayer is substantially impermeable to the potassium ion, and becomes at least partially permeable upon contact with the analyte.

5. The method of claim 1, including the step of coupling the detector to a transducer providing a measurable signal.

6. The method of claim 1, wherein the analyte is a vascular endothelial growth factor.

7. The method of claim 1, including the step of chemically modifying a permeable cellulose triacetate membrane to induce selectivity for the potassium ion.

8. The method of claim 7, including chemically modifying the cellulose triacetate membrane with valinomycin to induce selectivity for potassium.

9. A method for monitoring an analyte in a patient during a predetermined time interval, comprising:
   (1) obtaining a biological sample from a patient;
   (2) combining the biological sample with a predetermined amount of a potassium ion to form a mixture; and
   (3) contacting the mixture with a biosensor comprising: (a) a live endothelial or epithelial cell barrier which is substantially impermeable to the potassium ion, (b) a permeable membrane which is selective for the potassium ion, and (c) a detector capable of detecting the potassium ion;
   (4) detecting the presence or absence in the mixture of an analyte selected from at least one of a vascular endothe-

SEQUENCE LISTING

<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: synthetic RGD peptide sequence

<400> SEQUENCE: 1

Gly Arg Gly Asp Ser
1               5 lial growth factor, a basic fibroblast growth factor, a hepatocyte growth factor, and a tumor necrosis factor-α, wherein the analyte causes the live cell barrier to become at least partially permeable to the potassium ion whereby the potassium ion passes through the live cell barrier and the membrane and is detected by the detector;

(5) correlating the amount of the potassium ion detected with the quantity of the analyte in the biological sample; and (6) repeating steps 1 trough 5 after a predetermined time interval has passed.

10. The method of claim 9, including selecting the biological sample from the group consisting of serum, whole blood, plasma, a tissue biopsy, an organ biopsy, lymphatic fluid, saliva, tears, milk, urine, and any combination thereof.

11. The method of claim 9, wherein the live cell barrier comprises a transformed human endothelial cell line.

12. The method of claim 11, including providing the live cell barrier as a substantially confluent monolayer which is contiguous with the permeable membrane.

13. The method of claim 9, including coupling the detector to a transducer providing a detectable signal.

14. The method of claim 9, wherein the analyte is a vascular endothelial cell growth factor.

15. The method of claim 9, including the step of chemically modifying a permeable cellulose triacetate membrane to induce selectivity for the potassium ion.

16. The method of claim 15, including chemically modifying the cellulose triacetate membrane with valinomycin to induce selectivity for potassium.

* * * * *

UNITED STATES PATENT AND TRADEMARK OFFICE
CERTIFICATE OF CORRECTION

PATENT NO. : 7,595,149 B1  Page 1 of 1
APPLICATION NO. : 11/269363
DATED : September 29, 2009
INVENTOR(S) : Anderson et al.

It is certified that error appears in the above-identified patent and that said Letters Patent is hereby corrected as shown below:

Column 11, claim 9, line 11, change "trough" to --through--.

Signed and Sealed this

First Day of December, 2009

David J. Kappos
*Director of the United States Patent and Trademark Office*